United States Patent [19]
Geuder et al.

[11] Patent Number: 5,451,229
[45] Date of Patent: Sep. 19, 1995

[54] CANNULA FOR AN EYE-SURGERY INSTRUMENT

[75] Inventors: Volker Geuder, Heidelberg; Hans Geuder, Leimen; Dieter Frauenfeld, Heidelberg; Hans-Reinhard Koch, Bonn, all of Germany

[73] Assignee: Hans Geuder GmbH, Heidelberg, Germany

[21] Appl. No.: 231,378

[22] Filed: Apr. 22, 1994

[30] Foreign Application Priority Data

Apr. 23, 1993 [DE] Germany ............ 43 13 245.6

[51] Int. Cl.6 ............................................. A61B 17/32
[52] U.S. Cl. ..................................... 606/107; 604/902; 604/22
[58] Field of Search ............ 606/1, 107, 159, 167–171; 623/4, 6; 604/19, 22, 35, 264, 266, 268, 272, 275, 902

[56] References Cited

U.S. PATENT DOCUMENTS

| 3,470,867 | 10/1969 | Goldsmith | 604/272 |
|---|---|---|---|
| 4,335,718 | 6/1982 | Calabrese | 604/272 |
| 4,531,934 | 7/1985 | Kossousky et al. | 604/22 |
| 4,808,153 | 2/1989 | Parisi | 606/169 |
| 5,154,694 | 10/1992 | Kelman | 604/35 |
| 5,156,143 | 10/1992 | Bocquet et al. | 606/169 |
| 5,195,952 | 3/1993 | Solnit et al. | 604/902 |
| 5,213,569 | 5/1993 | Davis | 606/107 |
| 5,217,465 | 6/1993 | Steppe | 604/35 |
| 5,242,385 | 9/1993 | Strukel | 606/169 |

Primary Examiner—Stephen C. Pellegrino
Assistant Examiner—Glenn Dawson
Attorney, Agent, or Firm—Max Fogiel

[57] ABSTRACT

A cannula for an eye-surgery instrument, employed to shatter the lens of the eye by high-frequency oscillation and to suction out the fragments. It accommodates a suction channel with a section that is wider toward the tip of the cannula. The wider section (20) comprises at least two straight bores (8, 9, & 10), one wider than another, extending coaxial with the suction channel (7) into the cannula (1) from its tip (5). Fragments of the shattered lens accumulate in the bores in accordance with size, where they can be further fragmented by ultrasound.

7 Claims, 1 Drawing Sheet

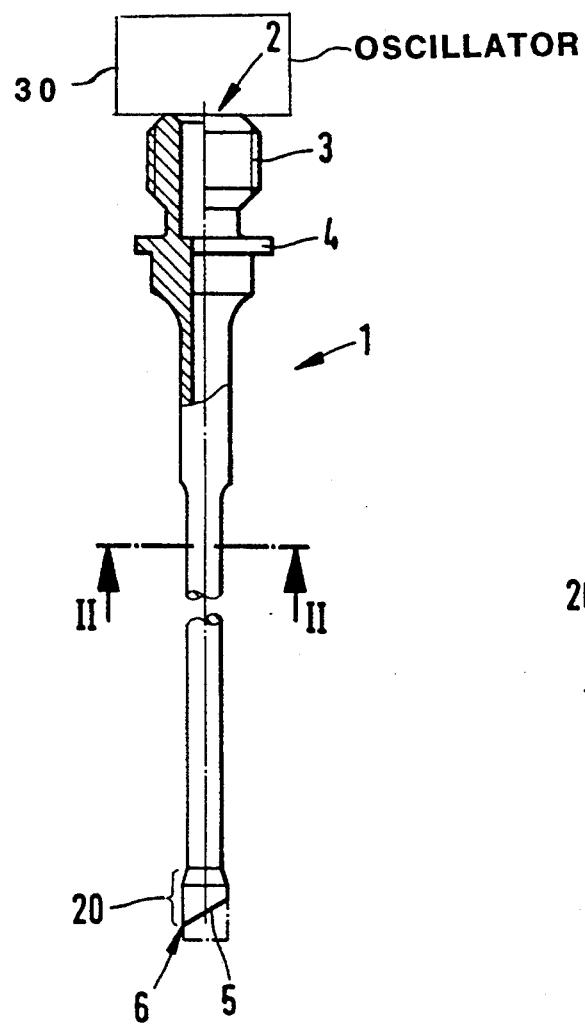
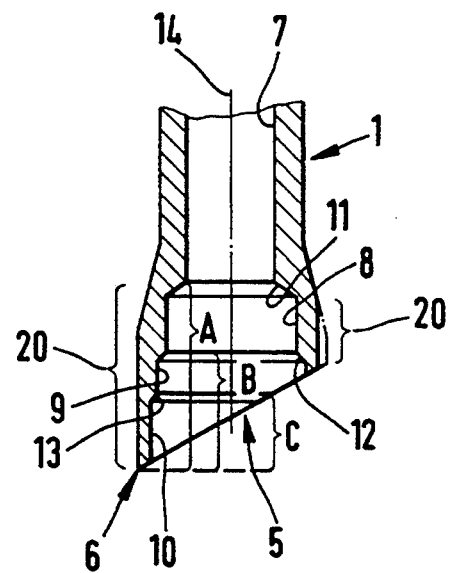
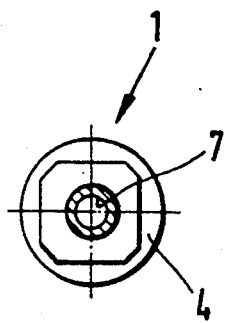
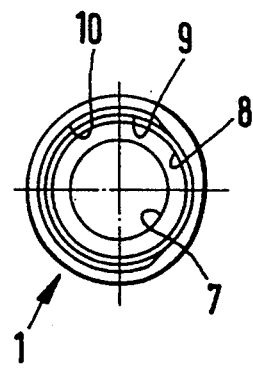

CANNULA FOR AN EYE-SURGERY INSTRUMENT

BACKGROUND OF THE INVENTION

The present invention concerns a cannula for an eye-surgery instrument. The cannula is employed to shatter the lens of the eye by high-frequency oscillation and to suction out the fragments. The cannula accommodates a suction channel with a section that is wider toward the tip of the cannula.

Cannulas of this type are known and have been demonstrated practical. A cannula of the genus is known from Ophthalmology Times 17, 14 (7/15/1992). The suction channel has an outward-tapering section that tapers conically in toward the suction channel from the aperture at the tip of the needle. The cannula acts on a lens that is to be removed by suctioning larger fragments into the wider opening at the cannula's point, breaking them up without risk to the rest of the eye by aiming a high-frequency ultrasonic wave at the conical surface, and suctioning the smaller fragments on out.

Cannulas with conically tapering sections require less high-frequency power to shatter a lens than cannulas without such sections do. The conical surfaces, however, can be produced only by complex procedures with special tools.

SUMMARY OF THE INVENTION

The object of the present invention is accordingly an improvement whereby a cannula with a wider section will be simpler and less expensive to manufacture.

This object is attained in the cannula in accordance with the present invention in that the wider section comprises at least two straight bores, one wider than the other, extending coaxial with the suction channel into the cannula from its tip.

Not many bores are needed for the wider section. They all extend axially and to different lengths, beginning with the open tip. The narrowest bore extends farthest. The wider bores extend in less and less. The resulting section will be gradually wider the nearer it is to the opening. The section can accordingly be produced by conventional boring tools.

Due to the gradually wider section, lens fragments of various size will become stuck at the transitions between the bores. The transitions will accordingly transmit the ultrasonic wave much more effectively to the fragments than they can be transmitted in the generic cannula with its conically tapering section. An especially more extensive surface will be exposed to the ultrasonic waves than is exposed at the state of the art if there are several graduations in width at the tip, with annular shoulders between them. The result will be a more rapid operation with much less ultrasonic output than at the state of the art, even when in accordance with one advanced version of the invention the transitions between the gradually-wider bores and/or the bores and the suction channel constitute conically tapering annular shoulders. These shoulders can be produced in the same step as the bores by the conical tip of the tool.

It will be practical for each gradually wider bore to extend to a different length.

The wider section in one preferred embodiment can include three bores.

BRIEF DESCRIPTION OF THE DRAWINGS

One embodiment of the invention will now be specified with reference to the schematic drawing, wherein FIG. 1 is a longitudinal partly sectional side view of a cannula with a beveled tip, FIG. 2 is a cross-section along the line II—II in FIG. 1, FIG. 3 is a larger-scale detail of the section in FIG. 1 through the beveled tip of the cannula, showing the wider section, and FIG. 4 is a tip-on view of the wider section of the cannula.

DESCRIPTION OF THE PREFERRED EMBODIMENTS

The cannula 1 illustrated in FIG. 1 is part of an eye-surgery instrument and is employed to shatter the lens of the eye and to remove the fragments once the sac has been opened.

Cannula 1 extends from a head 2 through a threaded connection 3 and a radially wider wrench accommodation 4 to a point 6 at tip 5. The cannula is attached to the unillustrated rest of the instrument at threaded connection 3.

Point 6 is inserted through an incision at the edge of the cornea and applied to the lens. The lens is then shattered by high-frequency axial oscillations of cannula 1, by an oscillator 30 with point 6 immediately against the lens. Any fragments of the lens are suctioned up through the cannula. A circular cross-section suction channel 7 extends as will be evident from FIG. 2 through cannula 1 from head 2 to tip 5.

Point 6 is produced at tip 5 by beveling it off, to approximately 30° in the present example. As will be evident from FIG. 3 the section 20 of suction channel 7 adjacent to tip 5 is wider. Extending coaxially out of section 20 are three bores 8, 9, and 10, each gradually wider than its predecessor toward tip 5 and coaxial with the central axis 14 of suction channel 7. The narrowest bore 8 is the farthest in. The next widest bore 9 is in the middle. The widest bore 10 is at point 6. Bores 8, 9, and 10 accordingly extend to various lengths A, B, and C toward suction channel 7 from the tip 5 of cannula 1. The wider the bore, the shorter it is.

At the transitions between bores 8, 9, and 10 and at the ends of the bores facing the suction channel 7 are annular shoulders 11, 12, and 13 between each bore and the next narrowest and accordingly tapering conically. The bore 8 adjacent to suction channel 7 has annular shoulder 11.

The walls of the bores 9 and 10 in the vicinity of the bevel do not extend all the way around. The wall of the bore 8 adjacent to suction channel 7 extends all the way around as will be evident from FIG. 4.

Bores 8, 9, and 10 differ in length, resulting in a wider section 20 that is long enough to accommodate larger fragments of lens. The fragments will accumulate in accordance with size at the annular shoulders 11, 12, and 13 in the associated bore, where they will be further fragmented by the ultrasonic wave propagating along suction channel 7. The gradually wider section 20 accordingly also has the function of transmitting the wave to and focusing it on the lens as a whole and its fragments.

We claim:

1. An eye-surgery instrument comprising: a cannula with a distal tip, oscillating means attached to said cannula for generating high-frequency oscillations to said cannula, said instrument being configured for shattering an eye lens by said high-frequency oscillations and suctioning out fragments occurring from said shattering; a suction channel in said cannula having a section widening toward said tip of the cannula, said widening section having at least two bores, one of said two bores being wider than the other bore, said suction channel having a remaining non-widening section, both of said bores having cross-sections wider than said remaining non-widening section, said bores extending coaxially with said suction channel into the cannula from said tip.

2. A cannula as defined in claim 1, wherein the wider bore is located distally of the other bore; and further including transitions between said bores comprising conically tapering annular shoulders.

3. A cannula as defined in claim 1, wherein the wider bore is located distally of the other bore; and further including a transition between said bores and said suction channel comprising a conically tapering annular shoulder.

4. A cannula as defined in claim 1, wherein each bore extends to a different length.

5. A cannula as defined in claim 1, wherein said widening section has three bores.

6. A cannula as defined in claim 1, wherein said bores are straight bores.

7. An eye-surgery instrument comprising: a cannula with a distal tip, oscillating means attached to said cannula for generating high-frequency oscillations to said cannula, said instrument being configured for shattering an eye lens by said high-frequency oscillations and suctioning fragments occurring from said shattering; a suction channel in said cannula having a section widening toward said tip of the cannula, said widening section having at least two bores, one of said two bores being wider than the other bore, said suction channel having a remaining non-widening section, both of said bores having cross-sections wider than said remaining non-widening section, said bores extending coaxially with said suction channel into the cannula from said tip; wherein the wider bore is located distally of the other bore, and further including transitions between said bores comprising conically tapering annular shoulders; each bore extending to a different length.

* * * * *